US006976340B2

(12) United States Patent
Schulze et al.

(10) Patent No.: US 6,976,340 B2
(45) Date of Patent: Dec. 20, 2005

(54) UNIVERSAL ACCESS PORT

(75) Inventors: James M. Schulze, Plymouth, MA (US); Kevin D. Ewing, Holland, MI (US); Clinton A. Peterson, Holland, MI (US); Richard L. Walker, Hudsonville, MI (US); Robert K. Hayes, Fruitport, MI (US)

(73) Assignee: Venturedyne Ltd., Milwaukee, WI (US)

( * ) Notice: Subject to any disclaimer, the term of this patent is extended or adjusted under 35 U.S.C. 154(b) by 181 days.

(21) Appl. No.: 10/310,358

(22) Filed: Dec. 5, 2002

(65) Prior Publication Data

US 2004/0110460 A1 Jun. 10, 2004

(51) Int. Cl.⁷ .............................. E08B 3/00
(52) U.S. Cl. .................. 52/208; 49/463; 52/173.2; 52/208; 414/217; 454/187
(58) Field of Search .................. 454/187; 52/198, 52/208, 173.2; 49/463, 465; 361/675; 414/217, 414/217.1

(56) References Cited

U.S. PATENT DOCUMENTS

| | | | | |
|---|---|---|---|---|
| 2,231,056 A | * | 2/1941 | De Mask | 361/675 |
| 4,854,726 A | | 8/1989 | Lesley et al. | 374/45 |
| 4,949,031 A | | 8/1990 | Szasz et al. | 324/158 |
| 5,147,136 A | | 9/1992 | Hartley et al. | 374/57 |
| 5,425,400 A | * | 6/1995 | Szatmary | 141/98 |
| 5,461,831 A | * | 10/1995 | Michal | 52/1 |
| 5,783,156 A | * | 7/1998 | Renzi et al. | 422/292 |
| 5,892,200 A | * | 4/1999 | Kendall et al. | 219/201 |
| 6,120,371 A | * | 9/2000 | Roberson et al. | 454/187 |
| 6,207,119 B1 | * | 3/2001 | Diccianni et al. | 422/295 |
| 6,225,554 B1 | * | 5/2001 | Trehan et al. | 174/35 MS |
| 6,303,854 B1 | * | 10/2001 | Papaleo et al. | 174/35 R |
| 6,347,490 B1 | * | 2/2002 | Spengler | 52/173.2 |
| 6,543,981 B1 | * | 4/2003 | Halsey et al. | 414/217.1 |
| 6,779,567 B1 | * | 8/2004 | Szatmary | 141/51 |

FOREIGN PATENT DOCUMENTS

EP 0 574893 A2 * 12/2003

* cited by examiner

*Primary Examiner*—Harold Joyce
(74) *Attorney, Agent, or Firm*—Jansson, Shupe, Munger & Antaramian, Ltd.

(57) ABSTRACT

A universal access port includes a specific size opening that is formed through a wall of a conditioning enclosure and located at a specific distance from a floor or mounting surface. The opening is preferably rectangular in shape, but other shapes may also be used. When not in use, the universal access port is covered with a sealing panel. Insertable devices may be efficiently inserted and removed from the universal access port. A perimeter of the insertable device is sized to be sealable inserted into the universal access port. Each insertable device preferably seals with an exterior and interior wall of the conditioning enclosure. Some insertable devices include fixturing devices, windows, manual manipulation devices, junction devices, hinged access doors, wire access devices, temperature modifying devices or air circulation devices.

5 Claims, 6 Drawing Sheets

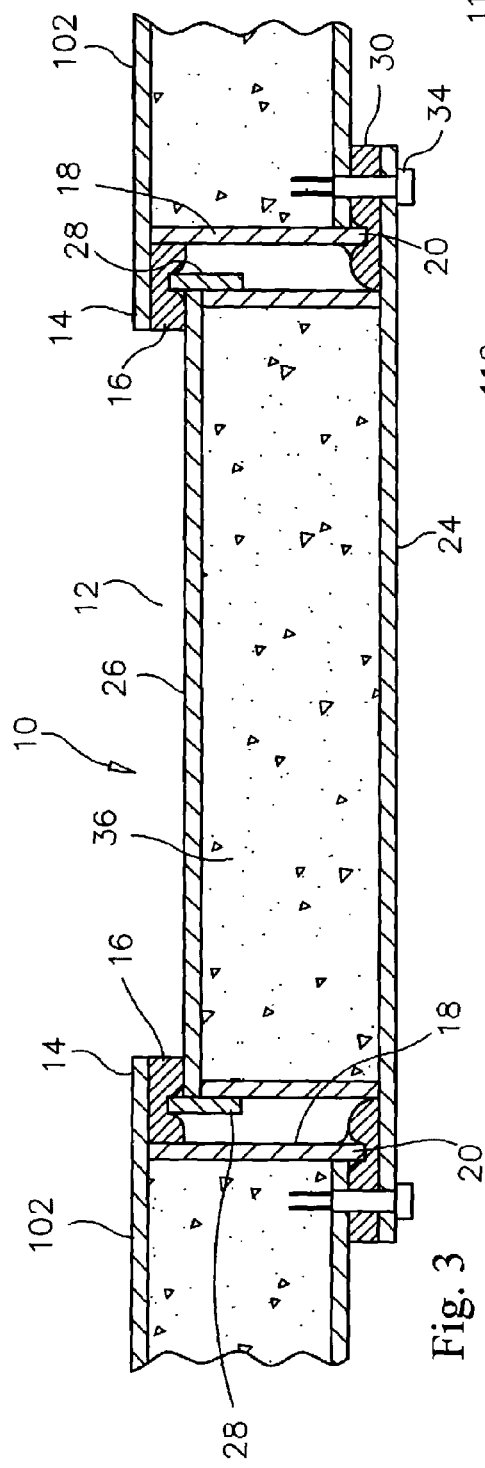
Fig. 3
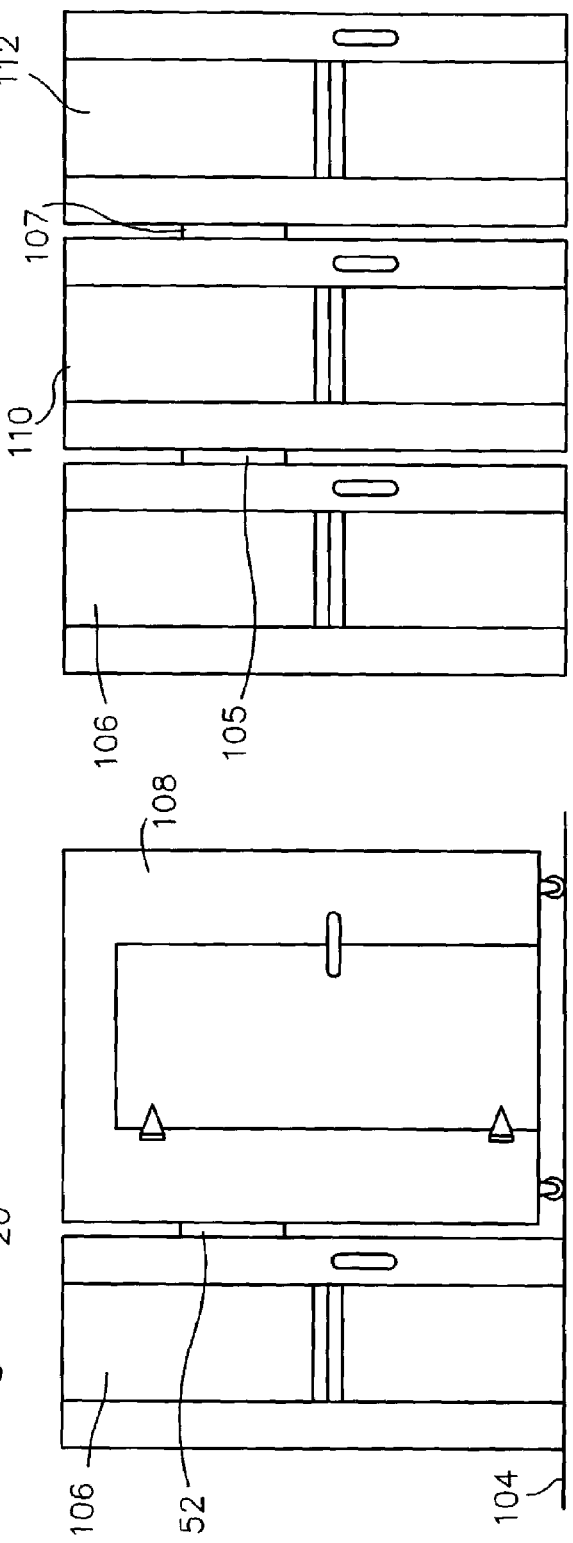
Fig. 8
Fig. 9

UNIVERSAL ACCESS PORT

BACKGROUND OF THE INVENTION

1. Field of the Invention

The present invention relates generally to conditioning enclosures and more specifically to a universal access port for conditioning enclosures, which is structured to receive numerous insertable devices.

2. Discussion of the Prior Art

There are several conditioning enclosures on the market, which disclose an opening created in a side thereof. A conditioning enclosure is defined as an oven, freezer, incubator, burn-in chamber, environmental test chamber, shaker, or any other device that stresses, modifies, or conditions an item inserted therein. U.S. Pat. No. 4,854,726 to Lesley et al. discloses a thermal stress screening system. An exposure chamber is connected to a cabinet with a pair of insulated delivery hoses. U.S. Pat. No. 4,949,031 to Szasz et al. discloses an environmental stress screening apparatus for electronic products. A product carrier pallet is inserted into an opening formed in an environmental test chamber. U.S. Pat. No. 5,147,136 to Hartley et al. discloses a temperature cycling test chambers. A portion of the wall is rotable between two different test chambers.

Accordingly, there is a clearly felt need in the art for a universal access port formed in a side of a conditioning enclosure, which has a specific size and shape to receive windows, wire access devices, bulkhead connectors, manual manipulation devices, doors, junction boxes, shelves, racks, drawers, blowers, a slave test chamber, and other insertable devices.

SUMMARY OF THE INVENTION

The present invention provides a universal access port for conditioning enclosures, which receives standard sized insertable devices, thus increasing the versatility of one or more conditioning enclosures. At least one universal access port allows a first conditioning enclosure to have expanded capacity by connecting additional conditioning enclosures to the first conditioning enclosure to retain the additional parts for testing. The additional conditioning enclosures would be connected with a junction device inserted into the universal access ports of each conditioning enclosure.

The additional conditioning enclosures are used as auxiliary units and their functionality need not be the same as the first conditioning enclosure. For example, the capacity for performing some type of temperature testing is increased without the cost of additional conditioning enclosures having the same function as the first conditioning enclosure. The universal access port also provides modular assembly of a group of conditioning units each having different functions. The function of each different conditioning unit may be activated when appropriate.

Each universal access port includes a specific size opening that is formed through a wall of a conditioning enclosure and located at a specific distance from a floor or mounting surface of the conditioning enclosure. The opening preferably has a rectangular shape, but other shapes may also be used. When not in use, the universal access port is covered with a sealing panel. Insertable devices may be efficiently inserted and removed from the universal access port, including the sealing panel. A perimeter of an insertable device is sized to be sealably inserted into the universal access port. Each insertable device preferably seals with an exterior and an interior wall of the conditioning enclosure. Some insertable devices include fixture devices, windows, manual manipulation devices, junction devices, hinged access doors, wire access devices, hydraulic connection devices, temperature modifying devices, air circulation devices, gas insertion devices, blower devices, or any other appropriate insertable device.

Accordingly, it is an object of the present invention to provide at least one universal access port in a conditioning enclosure, each universal access port has a specific opening size located a specified distance from a floor or mounting surface of the conditioning enclosure.

Finally, it is another object of the present invention to provide a plurality of insertable devices that are sized to be inserted into a universal access port formed in a conditioning enclosure.

These and additional objects, advantages, features and benefits of the present invention will become apparent from the following specification.

BRIEF DESCRIPTION OF THE DRAWINGS

FIG. 3 is a cross sectional view of a sealing panel attached to a universal access port of a conditioning enclosure in accordance with the present invention.

FIG. 8 is a front view of a first conditioning enclosure connected to a roll-up, walk-in conditioning chamber with a junction device in accordance with the present invention.

FIG. 9 is a front view of three conditioning enclosures connected together with two junction devices in accordance with the present invention.

DETAILED DESCRIPTION OF THE PREFERRED EMBODIMENTS

Figure 1:
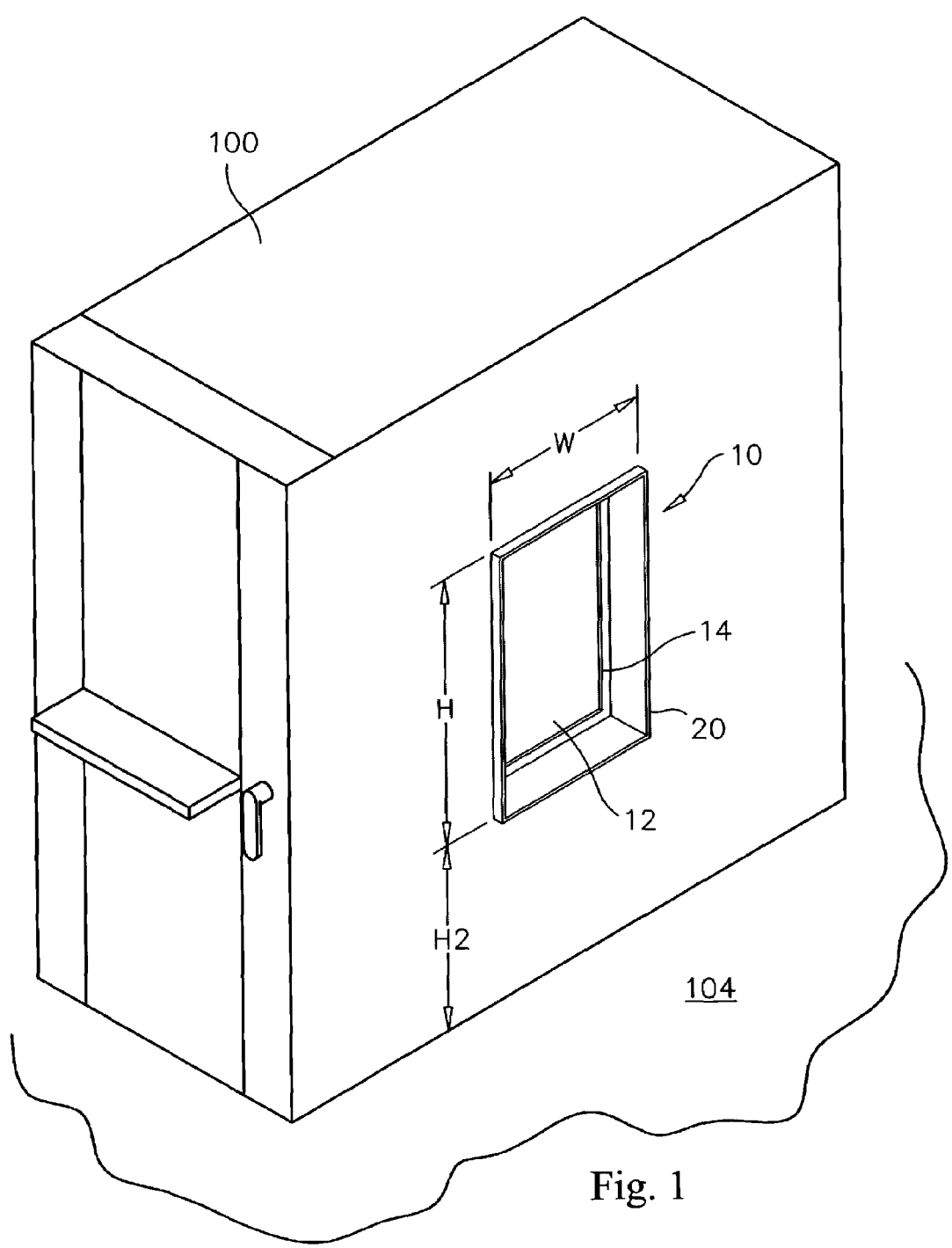
FIG. 1 is a perspective view of a conditioning enclosure with a universal access port in accordance with the present invention.

With reference now to the drawings, and particularly to FIG. 1, there is shown a perspective view of a conditioning enclosure 100 with a universal access port 10. With reference to FIG. 3, the universal access port 10 preferably includes an opening 12 of a specific width "W" and height "H" formed through a wall 102 of the conditioning enclosure 100. The universal access port 10 is disclosed as having a rectangular shape, but other shapes may also be used. Preferably, an interior peripheral flange 14 extends from an interior wall 102. The interior peripheral flange 14 surrounds the perimeter of the opening 12. A perimeter sealing gasket 16 is attached to the interior peripheral flange 14. Preferably, a perimeter sealing ridge 20 extends from a peripheral wall 18 of the opening 12. A bottom of the opening 12 is located at a height "H2" from a floor or mounting surface 104 of the conditioning enclosure 100.

Figure 2:
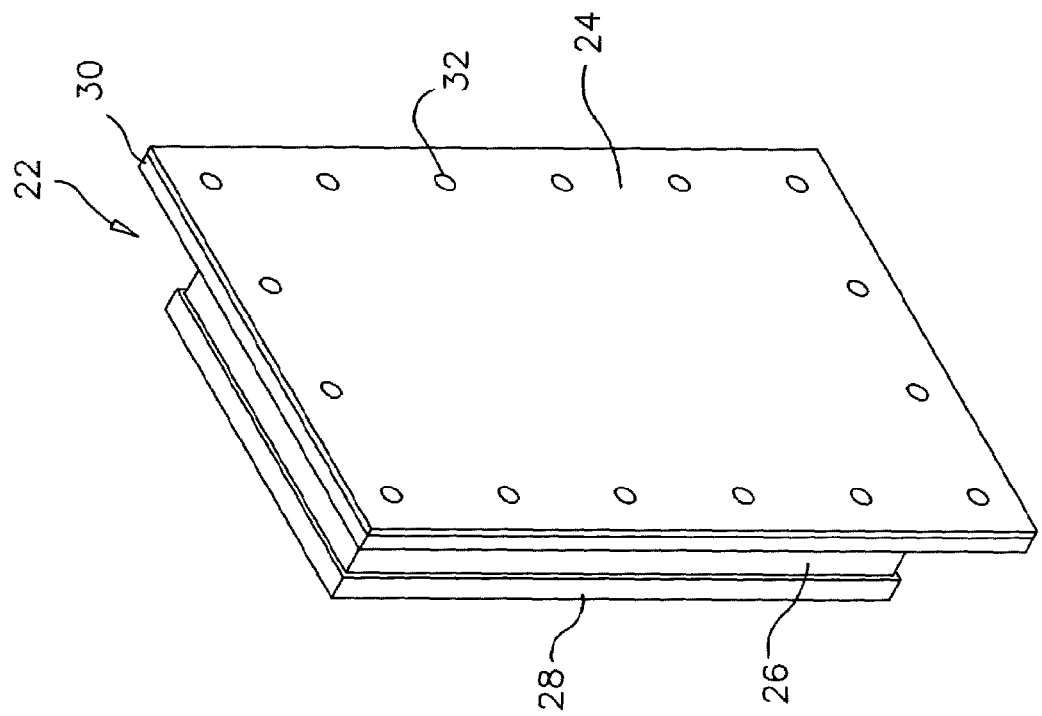
FIG. 2 is a perspective view of a sealing panel for insertion into a universal access port of a conditioning enclosure in accordance with the present invention.

With reference to FIG. 2, when not in use, the universal access port 10 is covered with a sealing panel 22. The sealing panel 22 preferably includes a mounting plate 24, an insulated insert 26, a panel perimeter sealing ridge 28, and a panel perimeter sealing gasket 30. A plurality of mounting holes 32 are formed near the perimeter of the mounting plate 24. A plurality of fasteners 34 are inserted through the plurality of mounting holes 32 to retain the sealing panel 22 in the universal access port 10. The insulated insert 26 extends form a back of the mounting plate 24. The insulated insert 26 preferably contains an equivalent amount of insulation 36 found in the walls 102 of the conditioning enclosure 100. The panel perimeter sealing ridge 28 is attached to a perimeter of the insulated insert 26. The panel perimeter sealing ridge 28 seals against the perimeter sealing gasket 16 and the perimeter sealing ridge 20 seals against the panel perimeter sealing gasket 30. One method of sealing the sealing panel 22 (and other insertable devices) to the universal access port 10 is disclosed; however other methods of sealing may also be used.

Figure 4:
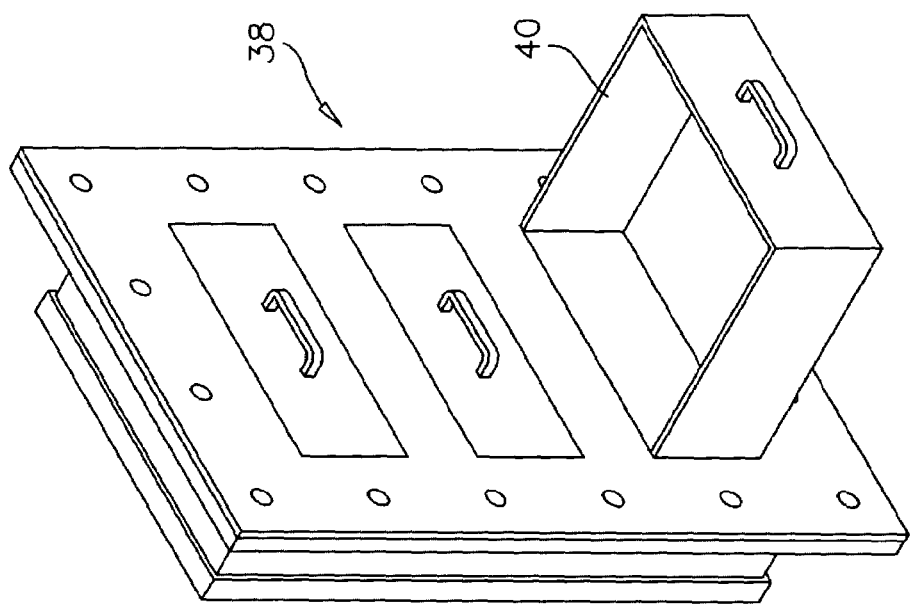
FIG. 4 is a perspective view of a drawer device for insertion into a universal access port of a conditioning enclosure in accordance with the present invention.

FIGS. 4–7 disclose sealing panels which have been modified to form insertable devices. FIG. 4 discloses a drawer device 38. A plurality of drawers 40 are slidably retained in the drawer device 38. The plurality of drawers 40 are capable of holding a plurality of small parts for environmental testing. The plurality of parts are placed in each drawer 40. A back of the drawer will be exposed to an inside atmosphere of an environmental chamber. The plurality of small parts are removed after the environmental testing has been performed. The drawer device 38 includes all of the sealing and attachment features of the sealing panel 22.

Figure 5:
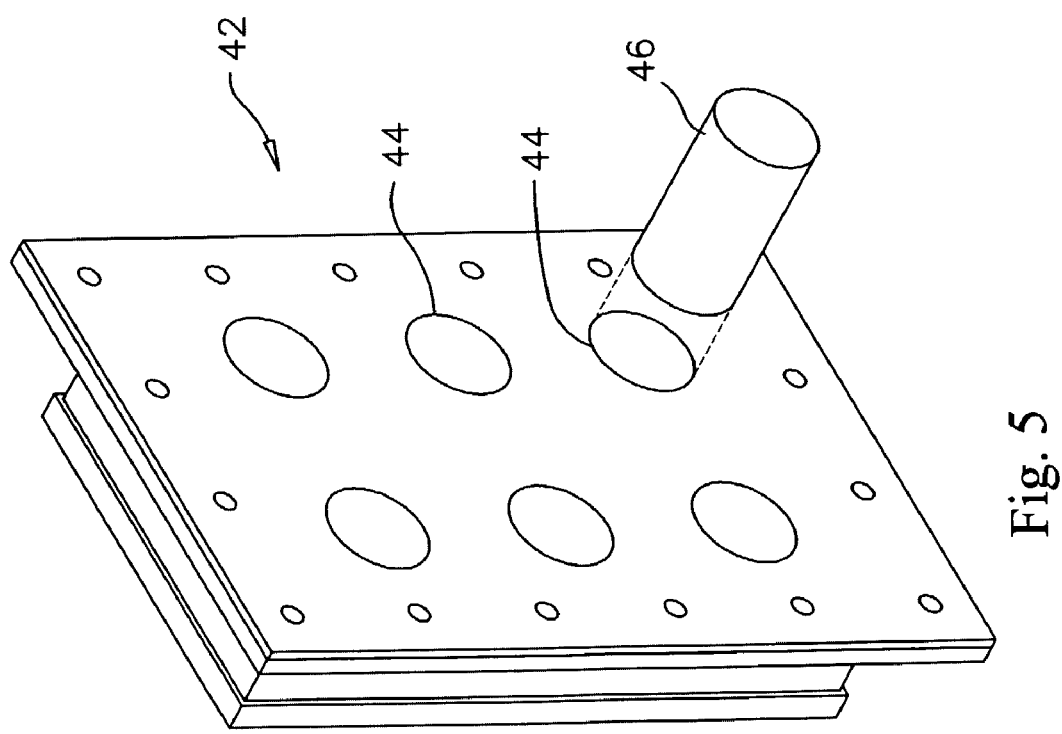
FIG. 5 is a perspective view of a wire access device for insertion into a universal access port of a conditioning enclosure in accordance with the present invention.

FIG. 5 discloses a wire device 42. A plurality of through passages 44 are formed through the wire device 42. Each through passage 44 is sized to firmly receive a single sealing insert 46. Each sealing insert 46 is preferably fabricated from foam, but other materials may also be used. Each sealing insert 46 is capable of sealing around wires or other lines that need to be run through the wall 102 of the conditioning enclosure 100. A round through passage 44 is disclosed, but the through passage may also have other shapes. The wire device 42 includes all of the sealing and attachment features of the sealing panel 22.

Figure 6A:
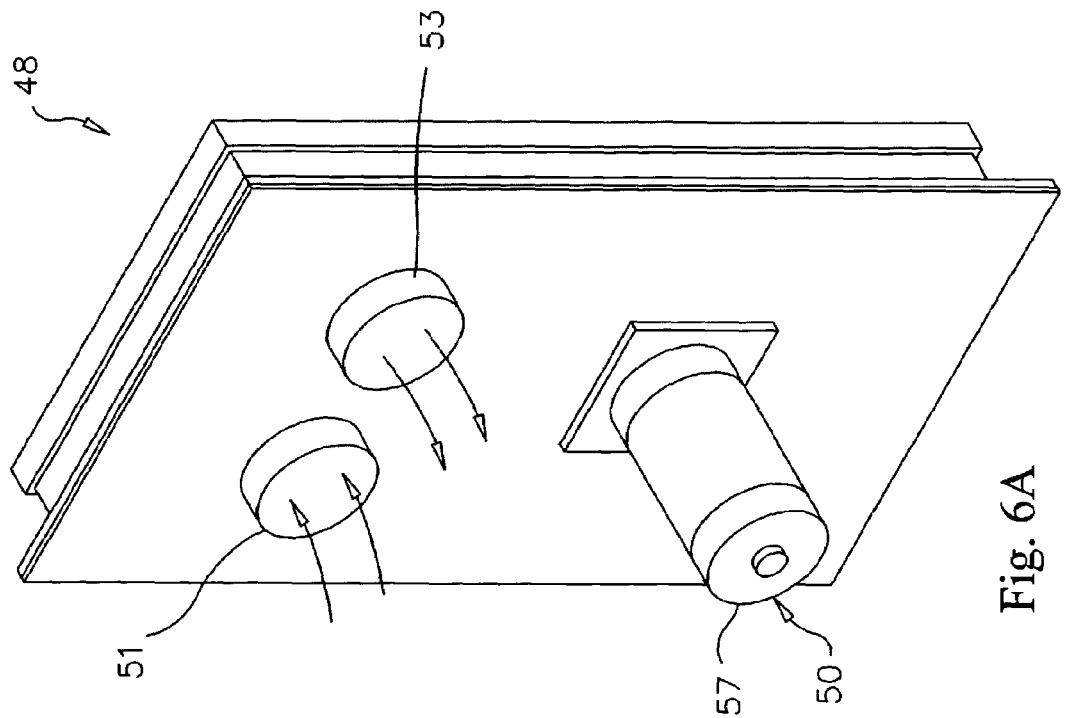
FIG. 6a is an exterior perspective view of a blower device for insertion into a universal access port of a conditioning enclosure in accordance with the present invention.
Figure 6:
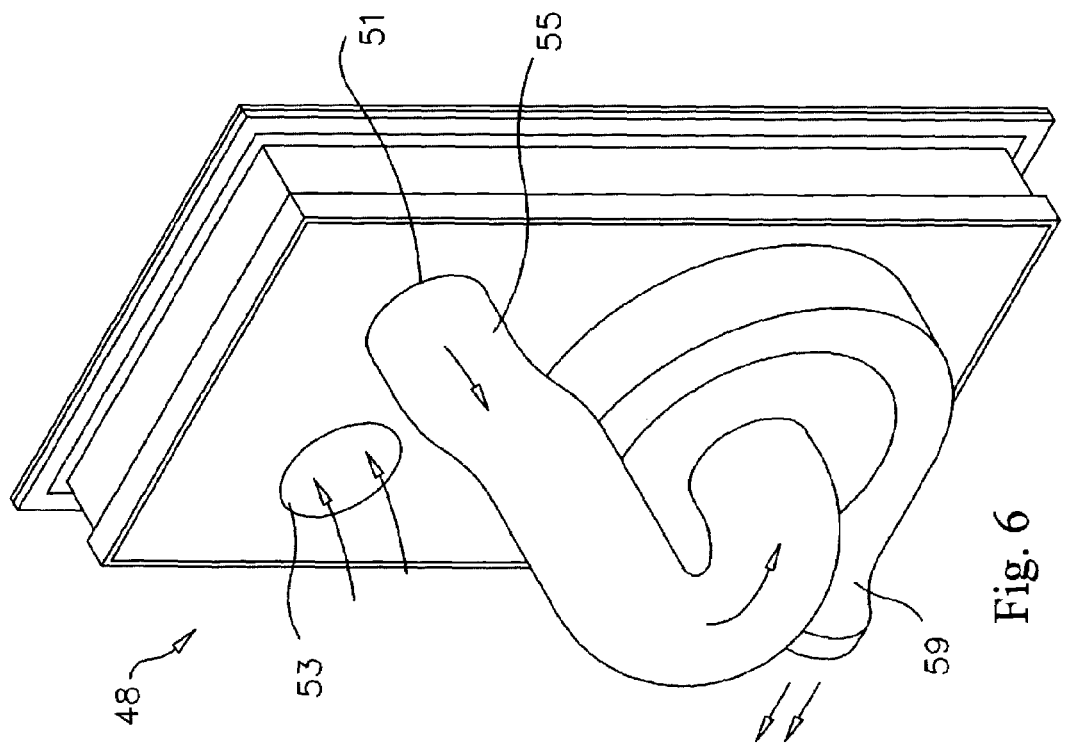
FIG. 6 is an interior perspective view of a blower device for insertion into a universal access port of a conditioning enclosure in accordance with the present invention.

FIGS. 6 and 6a disclose a blower device 48. The blower device 48 includes an air blower 50, an input port 51, an output port 53, and an input duct 55. The air blower 50 includes a motor 57 and an air impeller 59. An input duct (not shown) is preferably connected between a source of conditioned air and the input port 51. An output duct (not shown) is preferably connected between the source of conditioned air and the output port 53. The motor 57 turns a fan inside the air impeller 59 to draw air from the input port 51 through the input duct 55 to propelled conditioned air substantially perpendicular to the output port 53. The blower device 48 includes all of the sealing and attachment features of the sealing panel 22.

Figure 7:
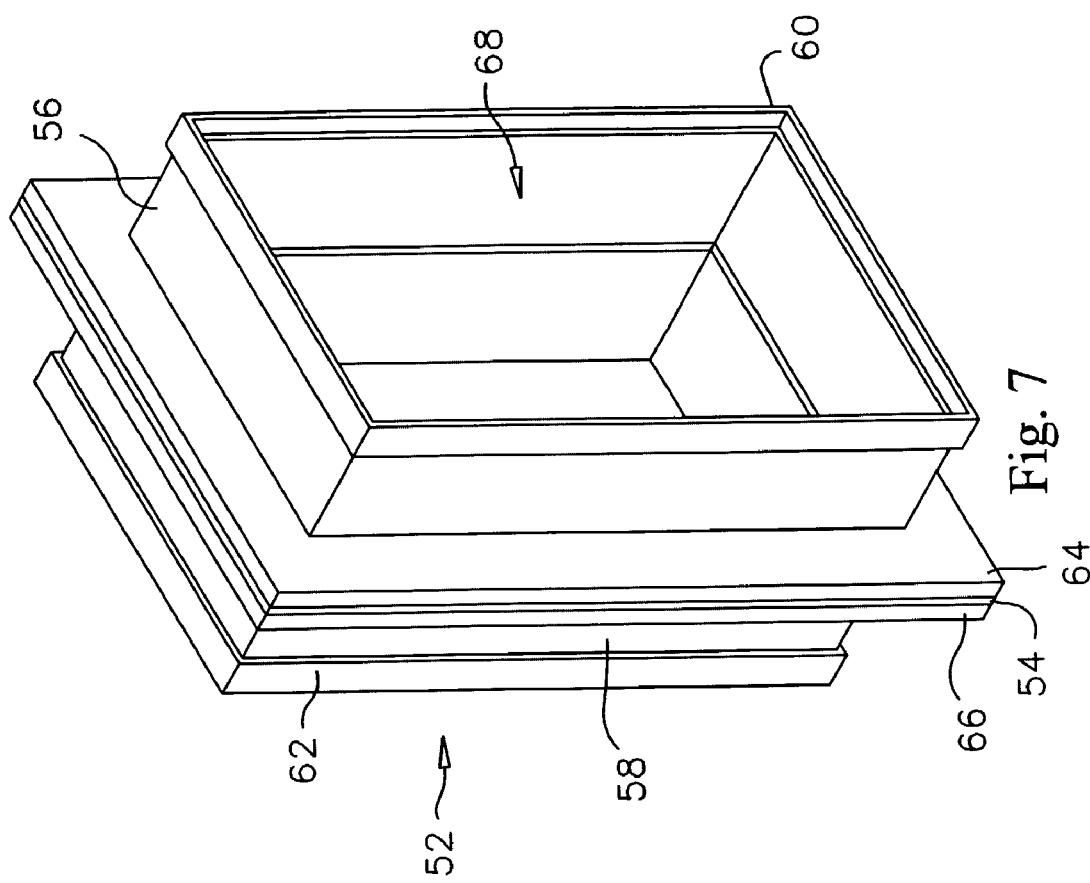
FIG. 7 is a perspective view of a junction device for insertion into universal access ports of two environmental test chambers in accordance with the present invention.

FIG. 7 discloses a junction device 52. The junction port device 52 includes a mounting plate 54, a first insulated insert 56, a second insulated insert 58, a first panel perimeter sealing ridge 60, a second perimeter panel sealing ridge 62, a first panel perimeter sealing gasket 64, and a second panel perimeter sealing ridge 66. The first insulated insert 56 extends from a first side of the mounting plate 54 and the second insulated insert 58 extends from a second side of the mounting plate 54. The first panel perimeter sealing ridge 60 is attached to a perimeter of the first insulated insert 56 and the second panel perimeter sealing ridge 62 is attached to a perimeter of the second insulated insert 58. The first panel perimeter sealing gasket 64 is attached to the first side of the mounting plate 54 and the second panel perimeter sealing gasket 66 is attached to the second side of the mounting plate 54. A through passage 68 is formed through the first insulated insert 56, the mounting plate 54 and the second insulated insert 58.

With reference to FIG. 8, the junction device 52 is used to connect a first conditioning enclosure 106 to a roll-up, walk-in conditioning enclosure 108. The first insulated insert 56 of the junction device 52 is inserted into a universal access port of the first conditioning enclosure 106 and a second insulated insert 58 of the junction device 52 is inserted into a universal access port of the roll-up, walk-in conditioning enclosure 108. The conditioning enclosures are pushed together to retain the junction device 52.

With reference to FIG. 9, three conditioning enclosures are connected in series with two junction devices. The first conditioning enclosure 106 is connected to one side of a second conditioning enclosure 110 with a first junction device 105 and a third conditioning enclosure 112 is connected to the other side of the second conditioning enclosure 110 with a junction device 107. The second conditioning enclosure 110 includes at least two universal access ports.

Figure 11:
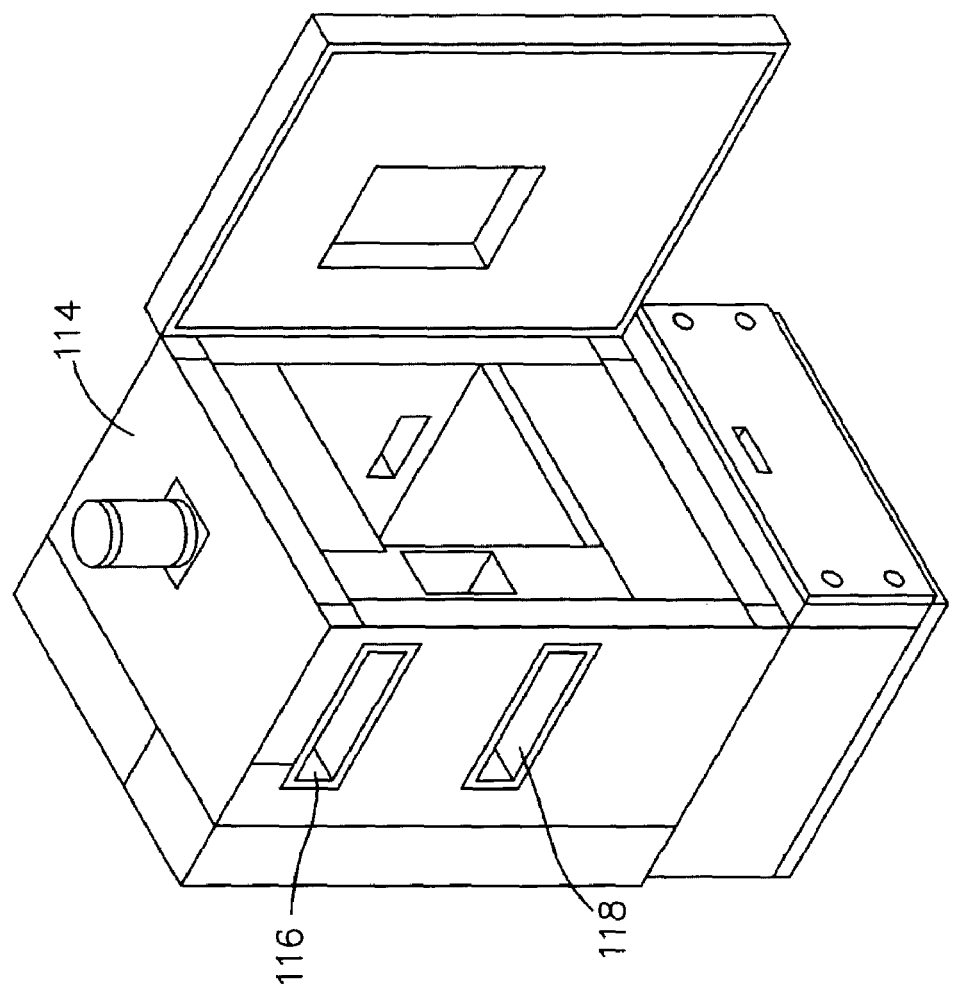
FIG. 11 is a perspective view of a conditioning enclosure with two dampers.
Figure 10:
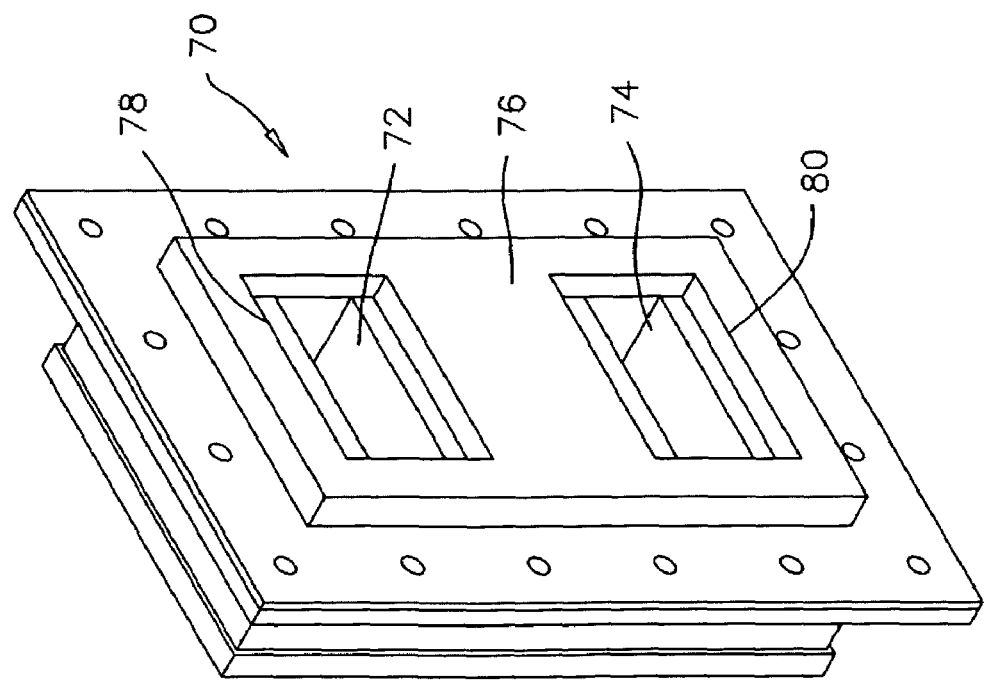
FIG. 10 is a perspective view of a damper device for insertion into a universal access port of one conditioning enclosure and mating with two dampers on another conditioning enclosure in accordance with the present invention.

FIG. 10 discloses a damper device 70. The damper device 70 includes a first damper through passage 72, a second damper through passage 74, and a sealing gasket 76. A first passage opening 78 is formed through the sealing gasket 76 to provide access to the first damper through passage 72. A second passage opening 80 is formed through the sealing gasket 76 to provide access to the first damper through passage 74. The damper device 70 includes all of the sealing and attachment features of the sealing panel 22. With reference to FIG. 11, a conditioning enclosure 114 is disclosed with a first damper 116 and a second damper 118 disposed on a side thereof. The damper device 70 is attached to the universal access port of a first conditioning enclosure (not shown). The conditioning enclosure 118 will be pushed against the sealing gasket 76, such that the first passage opening 78 is aligned with the first damper 116 and the second passage opening 80 is aligned with the second damper 118.

Several types of insertable devices are disclosed, but the invention should include other types of insertable devices, which already exist or may be created in the future.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of increasing the versatility of a conditioning enclosure, comprising the steps of:

forming at least one opening through a wall of said conditioning enclosure, each opening having a specific shape and size, said conditioning enclosure stressing or modifying at least one item inserted therein for testing purposes;

locating said opening a specific distance from a floor or mounting surface of said conditioning enclosure;

making said specific shape, specific size, and said specific distance a standard opening for a plurality of conditioning enclosures; and providing an insertable junction device sized to be received by each opening said insertable junction device including a mounting plate, a first insulated insert extending from a front of said mounting plate and a second insulated insert extending from a rear of said mounting plate, forming a through passage through said mounting plate, said first insulated insert and said second insulated insert.

2. A method of increasing the versatility of a conditioning enclosure, comprising the steps of:

forming an opening through a wall of said conditioning enclosure, said opening having a specific shape and size, said conditioning enclosure stressing or modifying at least one item inserted therein for testing purposes;

locating said opening a specific dimension from a floor or mounting surface of said conditioning enclosure;

making said specific share, specific size, and said specific dimension of said opening a standard for a plurality of conditioning enclosures;

providing an insertable junction device that is sized to be received by said opening; and sealing said insertable junction device to said opening said insertable junction device including a mounting plate, a first insulated insert extending from a front of said mounting plate and a second insulated insert extending from a rear of said mounting plate, forming a through passage through said mounting plate, said first insulated insert and said second insulated insert.

3. A method of increasing the versatility of a conditioning enclosure, comprising the steps of:

forming at least one opening through a wall of said conditioning enclosure, each opening having a specific shape and size, said conditioning enclosure stressing or modifying at least one item inserted therein for testing purposes, each opening being sized to receive an insertable device;

locating said opening a specific distance from a floor or mounting surface of said conditioning enclosure; and making said specific shape, specific size, and said specific distance a standard for a plurality of conditioning enclosures;

providing a junction device for said insertable device, said junction device including a mounting plate, a first insulated insert extending from a front of said mounting plate and a second insulated insert extending from a rear of said mounting plate, forming a through passage through said mounting plate, said first insulated insert and said second insulated insert.

4. The method of claim 3, further comprising connecting the respective openings of two of the plurality of conditioning enclosures via said junction device.

5. The method of increasing the versatility of a conditioning enclosure of claim 3, further comprising the step of:

forming a sealing gasket on a perimeter of each one of said at least one opening at an interior end thereof, forming a sealing ridge on a perimeter of said opening at an exterior end thereof.

* * * * *